United States Patent
Arai et al.

(10) Patent No.: US 11,911,209 B2
(45) Date of Patent: Feb. 27, 2024

(54) IMAGING MEMBER, CONTROL DEVICE, MEDICAL IMAGING SYSTEM, IMAGING METHOD, CONTROL METHOD, AND CONTROL PROGRAM

(71) Applicant: FUJIFILM CORPORATION, Tokyo (JP)

(72) Inventors: Takahisa Arai, Kanagawa (JP); Hiroki Nakayama, Kanagawa (JP); Yoshie Fujimoto, Kanagawa (JP); Shunsuke Kodaira, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 18/057,603

(22) Filed: Nov. 21, 2022

(65) Prior Publication Data
US 2023/0099356 A1    Mar. 30, 2023

Related U.S. Application Data

(62) Division of application No. 16/802,567, filed on Feb. 27, 2020, now abandoned.

(30) Foreign Application Priority Data

Mar. 29, 2019 (JP) .................. 2019-067290

(51) Int. Cl.
*A61B 8/00* (2006.01)
*A61B 8/08* (2006.01)
(Continued)

(52) U.S. Cl.
CPC ............ *A61B 8/0825* (2013.01); *A61B 8/403* (2013.01); *A61B 8/4281* (2013.01);
(Continued)

(58) Field of Classification Search
CPC ..... A61B 8/0825; A61B 8/403; A61B 8/4281; A61B 8/4263
See application file for complete search history.

(56) References Cited

U.S. PATENT DOCUMENTS 5,152,294 A    10/1992  Mochizuki et al.
9,636,073 B2 *  5/2017  Evans ................. A61B 8/4416
(Continued)

FOREIGN PATENT DOCUMENTS

DE    19926446 A1    1/2000
JP    2009-82399 A    4/2009

OTHER PUBLICATIONS

Extended European Search Report dated Aug. 7, 2020, issued in corresponding EP Patent Application No. 20160512.8.
(Continued)

*Primary Examiner* — Colin T. Sakamoto
(74) *Attorney, Agent, or Firm* — SOLARIS Intellectual Property Group, PLLC

(57) ABSTRACT

An imaging member including: a pressing member that presses a breast of a subject; and an ultrasonography member that has a first surface on which an acoustic matching member having fluidity is provided, and is provided such that a second surface on a side opposite to the first surface is provided on a surface of the pressing member, which is on a side opposite to a surface that comes into contact with the breast, via a coupling material having lower fluidity than the acoustic matching member.

9 Claims, 11 Drawing Sheets

(51) Int. Cl.
*A61B 6/00* (2006.01)
*A61B 6/04* (2006.01)

(52) U.S. Cl.
CPC .......... *A61B 8/4416* (2013.01); *A61B 6/0414* (2013.01); *A61B 6/4417* (2013.01); *A61B 6/502* (2013.01); *A61B 8/429* (2013.01)

(56) References Cited

U.S. PATENT DOCUMENTS

| | | | |
|---|---|---|---|
| 9,833,204 B2* | 12/2017 | Nanke | A61B 8/0825 |
| 9,949,719 B2* | 4/2018 | Zhang | A61B 6/025 |
| 11,013,478 B2* | 5/2021 | Radicke | A61B 8/0825 |
| 11,399,789 B2* | 8/2022 | Hoernig | A61B 6/502 |
| 2002/0068871 A1 | 6/2002 | Mendlein et al. | |
| 2005/0288581 A1 | 12/2005 | Kapur et al. | |
| 2009/0268865 A1 | 10/2009 | Ren et al. | |
| 2010/0030078 A1 | 2/2010 | Mikami | |
| 2013/0116570 A1 | 5/2013 | Carson et al. | |
| 2014/0180082 A1* | 6/2014 | Evans | A61B 6/502 |
| | | | 600/436 |
| 2015/0351706 A1* | 12/2015 | Nanke | A61B 6/0414 |
| | | | 128/845 |
| 2016/0166234 A1* | 6/2016 | Zhang | A61B 8/4209 |
| | | | 600/443 |
| 2017/0245823 A1 | 8/2017 | Arai et al. | |
| 2017/0281124 A1 | 10/2017 | Arai et al. | |
| 2018/0368796 A1* | 12/2018 | Hoernig | A61B 6/502 |
| 2020/0060633 A1* | 2/2020 | Radicke | A61B 6/4417 |

OTHER PUBLICATIONS

Requirement for Restriction/Election issued by USPTO dated Jul. 23, 2021, in related U.S. Appl. No. 16/802,567.
Non-Final Office Action issued by USPTO dated Oct. 8, 2021, in related U.S. Appl. No. 16/802,567.
Final Office Action issued by USPTO dated Apr. 4, 2022, in related U.S. Appl. No. 16/802,567.
Advisory Action issued by USPTO dated Jul. 5, 2022, in related U.S. Appl. No. 16/802,567.
Non-Final Office Action issued by USPTO dated Aug. 30, 2022, in related U.S. Appl. No. 16/802,567.

* cited by examiner

IMAGING MEMBER, CONTROL DEVICE, MEDICAL IMAGING SYSTEM, IMAGING METHOD, CONTROL METHOD, AND CONTROL PROGRAM

CROSS-REFERENCE TO RELATED APPLICATIONS

The present application is a divisional application of U.S. application Ser. No. 16/802,567, filed on Feb. 27, 2020, and claims priority to Japanese Patent Application No. 2019-067290, filed on Mar. 29, 2019. Each of the above applications is hereby expressly incorporated by reference, in its entirety, into the present application.

BACKGROUND

Technical Field

The present disclosure relates to an imaging member, a control device, a medical imaging system, an imaging method, a control method, and a control program.

Related Art

A radiography apparatus has been known which irradiates an object, such as the breast of a subject, with radiation emitted from a radiation source and detects the radiation transmitted through the object with a radiation detector to capture a radiographic image.

In addition, an ultrasonography apparatus has been known which scans the breast of a subject with ultrasonic waves by moving an ultrasound probe along the breast to capture an ultrasound image of the breast. JP2009-082399A discloses an apparatus that can capture both a radiographic image and an ultrasound image of the breast.

JP2009-082399A discloses a technique of reducing an influence of echo jelly, which is applied on a pressing plate that presses the breast and is used in capturing an ultrasound image, on a radiographic image by uniformly applying the echo jelly on the pressing plate.

In a case where the capture of an ultrasound image using an acoustic matching member, which is applied on a pressing plate that comes into contact with the breast and is for improving the scanning performance of an ultrasound probe, is ended and then the capture of a radiographic image using the pressing plate on which the acoustic matching member has been applied, by the same radiography apparatus is scheduled, a radiographic image cannot be continuously captured until the acoustic matching member applied to the pressing plate that comes into contact with the breast is wiped. As a result, imaging efficiency is decreased in some cases.

SUMMARY

The present disclosure has been made in view of the above-described circumstances, and an object of the present disclosure is to provide an imaging member, a control device, a medical imaging system, an imaging method, a control method, and a control program which can improve imaging efficiency.

In order to achieve the object, an imaging member according to a first aspect of the present disclosure comprises a pressing member that presses a breast of a subject; and an ultrasonography member that has a first surface on which an acoustic matching member having fluidity is provided, and is provided such that a second surface on a side opposite to the first surface is provided on a surface of the pressing member, which is on a side opposite to a surface that comes into contact with the breast, via a coupling material having lower fluidity than the acoustic matching member.

In an imaging member according to a second aspect of the present disclosure, in the imaging member according to the first aspect, a size of the second surface of the ultrasonography member is smaller than a size of the surface of the pressing member which is on the side opposite to the surface that comes into contact with the breast.

In an imaging member according to a third aspect of the present disclosure, in the imaging member according to the first or second aspect, in the ultrasonography member, a projection extending in a side opposite to the second surface is provided on a side corresponding to a chest wall side of the subject and a pair of facing sides intersecting the side corresponding to the chest wall side, of the first surface.

In an imaging member according to a fourth aspect of the present disclosure, in the imaging member according to any one of the first to third aspects, the ultrasonography member is fixed to the pressing member.

An imaging member according to a fifth aspect of the present disclosure, in the imaging member according to any one of the first to third aspects, further includes a fixture that fixes the pressing member and the ultrasonography member.

In an imaging member according to a sixth aspect of the present disclosure, in the imaging member according to any one of the first to fifth aspects, each of the pressing member and the ultrasonography member is provided with a mark for positioning of the pressing member and the ultrasonography member.

In order to achieve the object, a control device according to a seventh aspect of the present disclosure comprises a radiography control unit that performs control of irradiating a breast which is in a pressed state by the pressing member of the imaging member according to any one of the first to sixth aspects with radiation and causing a radiation detector to capture a radiographic image of the breast; and an ultrasonography control unit that performs control of causing an ultrasonography apparatus to capture an ultrasound image of the breast in a state where the ultrasonography member is provided on the surface of the pressing member which is on the side opposite to the surface that comes into contact with the breast, via the coupling material having lower fluidity than the acoustic matching member and the acoustic matching member is provided on the first surface of the ultrasonography member.

In a control device according to an eighth aspect of the present disclosure, in the control device according to the seventh aspect, the radiography control unit performs control of prohibiting capture of the radiographic image in a case where the ultrasonography member is provided on the surface of the pressing member which is on the side opposite to the surface that comes into contact with the breast.

In a control device according to a ninth aspect of the present disclosure, in the control device according to the seventh aspect, the radiography control unit performs control of warning against capture of the radiographic image in a case where the ultrasonography member is provided on the surface of the pressing member which is on the side opposite to the surface that comes into contact with the breast.

In a control device according to a tenth aspect of the present disclosure, in the control device according to the seventh aspect, the radiography control unit performs control of prohibiting that the ultrasonography member is provided on the surface of the pressing member which is on the side opposite to the surface that comes into contact with the breast, before capture of the radiographic image.

In a control device according to an eleventh aspect of the present disclosure, in the control device according to any one of the seventh to tenth aspects, the ultrasonography control unit performs control of prohibiting capture of the ultrasound image in a case where the ultrasonography member is not provided on the surface of the pressing member which is on the side opposite to the surface that comes into contact with the breast.

In a control device according to a twelfth aspect of the present disclosure, in the control device according to any one of the seventh to eleventh aspects, the ultrasonography control unit performs control of warning against capture of the ultrasound image in a case where the ultrasonography member is not provided on the surface of the pressing member which is on the side opposite to the surface that comes into contact with the breast.

In a control device according to a thirteenth aspect of the present disclosure, in the control device according to any one of the seventh to twelfth aspects, the ultrasonography control unit performs control of prohibiting capture of the ultrasound image in a case where the coupling material is not provided between the ultrasonography member and the surface of the pressing member which is on the side opposite to the surface that comes into contact with the breast.

In order to achieve the object, a medical imaging system according to a fourteenth aspect of the present disclosure comprises a mammography apparatus that causes a radiation detector to capture a radiographic image of a breast which is in a pressed state by the pressing member of the imaging member according to any one of the first to sixth aspects; an ultrasonography apparatus that captures an ultrasound image of the breast being in the pressed state by the pressing member and the ultrasonography member of the imaging member; and the control device according to any one of the seventh to thirteenth aspects, which controls capture of the radiographic image by the mammography apparatus and capture of the ultrasound image by the ultrasonography apparatus.

In order to achieve the object, a medical imaging system according to a fifteenth aspect of the present disclosure comprises a medical imaging apparatus that causes a radiation detector to capture a radiographic image of a breast which is in a pressed state by the pressing member of the imaging member according to any one of the first to sixth aspects, and causes an ultrasonography apparatus to capture an ultrasound image of the breast being in the pressed state by the pressing member and the ultrasonography member of the imaging member; and the control device according to any one of the seventh to thirteenth aspects, which controls capture of the radiographic image by the medical imaging apparatus and capture of the ultrasound image by the ultrasonography apparatus.

In order to achieve the object, an imaging method according to a sixteenth aspect of the present disclosure is an imaging method using the pressing member of the imaging member according to any one of the first to sixth aspects, and the imaging method comprises a step of causing a breast to be in a pressed state by the pressing member; a step of irradiating the breast in the pressed state with radiation and causing a radiation detector to capture a radiographic image; providing the ultrasonography member on the surface of the pressing member which is on the side opposite to the surface that comes into contact with the breast, via the coupling material having lower fluidity than the acoustic matching member; and a step of causing an ultrasonography apparatus to capture an ultrasound image after providing the acoustic matching member on the ultrasonography member.

In order to achieve the object, a control method according to a seventeenth aspect of the present disclosure is a control method for a computer to execute a process comprising: performing control of irradiating a breast which is in a pressed state by the pressing member of the imaging member according to any one of the first to sixth aspects with radiation and causing a radiation detector to capture a radiographic image of the breast; and performing control of causing an ultrasonography apparatus to capture an ultrasound image of the breast in a state where the ultrasonography member is provided on the surface of the pressing member which is on the side opposite to the surface that comes into contact with the breast, via the coupling material having lower fluidity than the acoustic matching member and the acoustic matching member is provided on the first surface of the ultrasonography member.

In order to achieve the object, a control program according to an eighteenth aspect of the present disclosure causes a computer to execute a process comprising: performing control of irradiating a breast which is in a pressed state by the pressing member of the imaging member according to any one of the first to sixth aspects with radiation and causing a radiation detector to capture a radiographic image of the breast; and performing control of causing an ultrasonography apparatus to capture an ultrasound image of the breast in a state where the ultrasonography member is provided on the surface of the pressing member which is on the side opposite to the surface that comes into contact with the breast, via the coupling material having lower fluidity than the acoustic matching member and the acoustic matching member is provided on the first surface of the ultrasonography member.

A control device according to an embodiment of the present disclosure is a control device including a processor and a memory, and the processor performs control of irradiating the breast which is in a pressed state by the pressing member of the imaging member according to any one of the first to sixth aspects with radiation and causing the radiation detector to capture a radiographic image of the breast; and performs control of causing an ultrasonography apparatus to capture an ultrasound image of the breast in a state where the ultrasonography member is provided on the surface of the pressing member which is on the side opposite to the surface that comes into contact with the breast, via the coupling material having lower fluidity than the acoustic matching member and the acoustic matching member is provided on the first surface of the ultrasonography member.

According to the present disclosure, it is possible to improve imaging efficiency.

DESCRIPTION OF EMBODIMENTS

Hereinafter, embodiments of the invention will be described in detail with reference to the drawings. The embodiments do not limit the invention.

Figure 1:
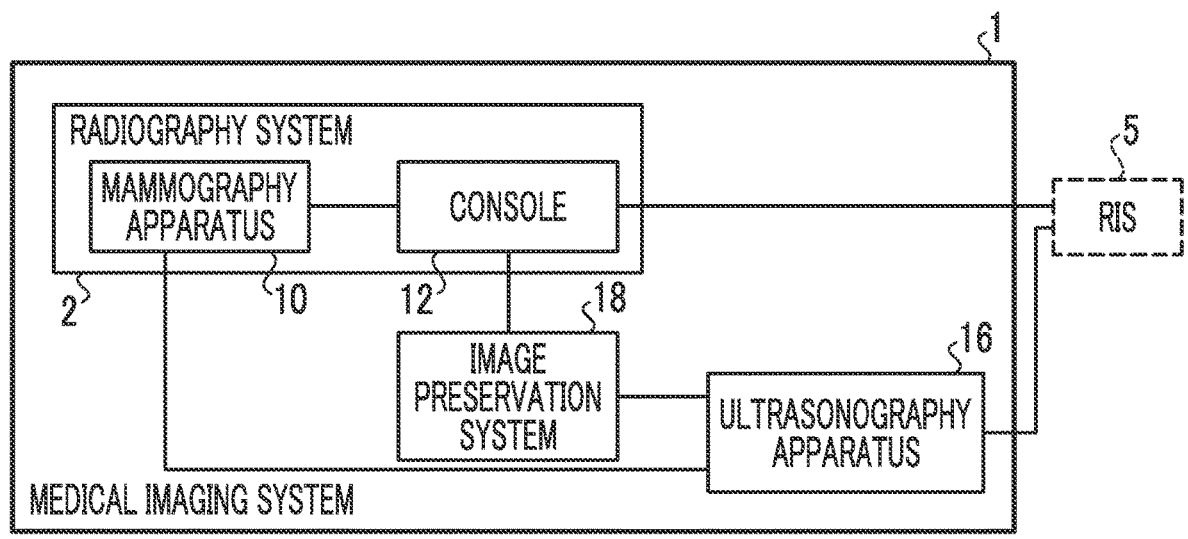
FIG. 1 is a configuration diagram schematically illustrating an example of the overall configuration of a medical imaging system of an embodiment.

First, an example of the overall configuration of a medical imaging system of the embodiment will be described. FIG. 1 is a configuration diagram illustrating an example of the overall configuration of a medical imaging system 1 of the embodiment.

As illustrated in FIG. 1, the medical imaging system 1 of the embodiment comprises a radiography system 2, an ultrasonography apparatus 16, and an image preservation system 18.

Figure 2:
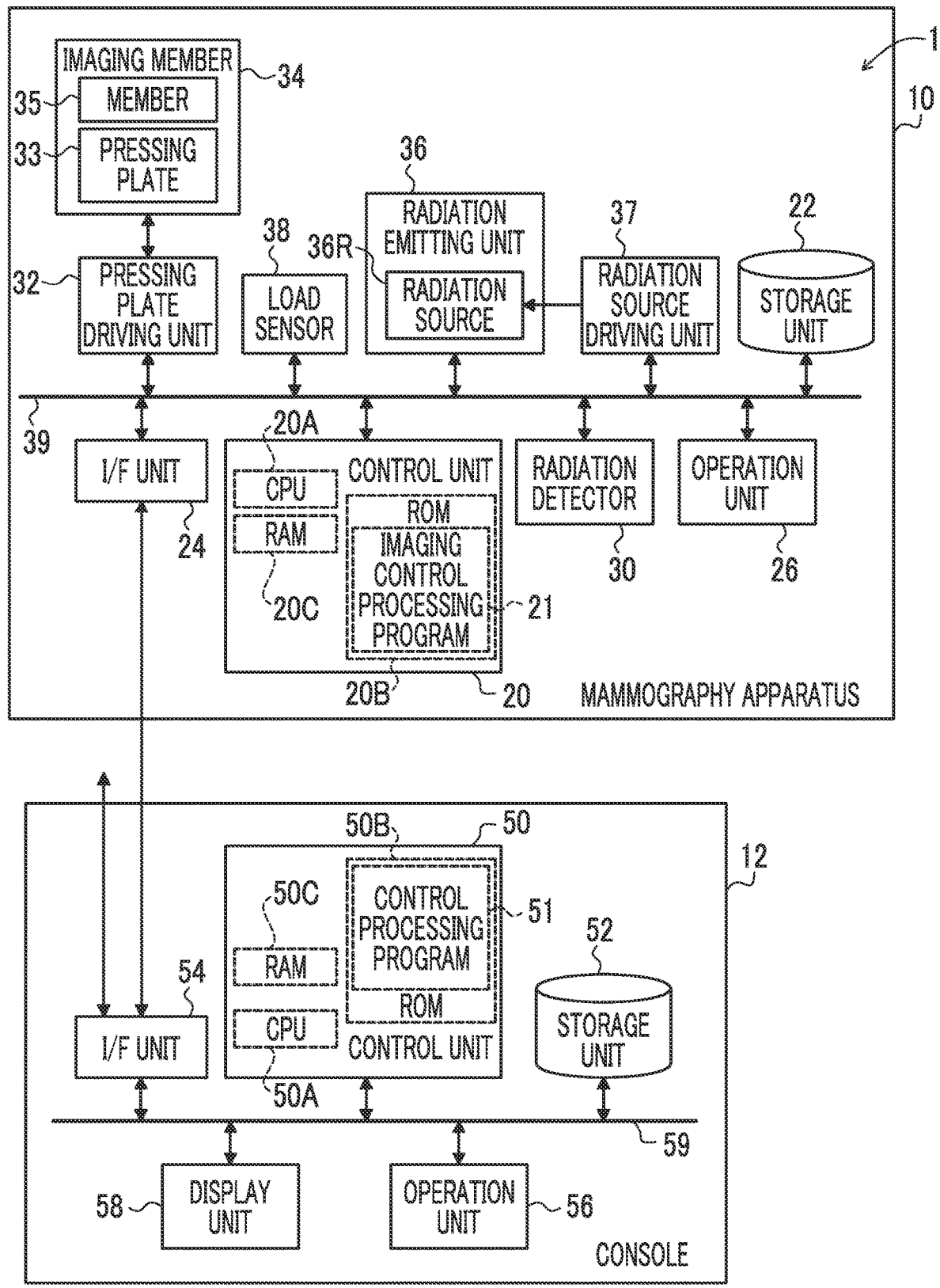
FIG. 2 is a block diagram illustrating an example of the configuration of a console and a mammography apparatus of the embodiment.
Figure 3:
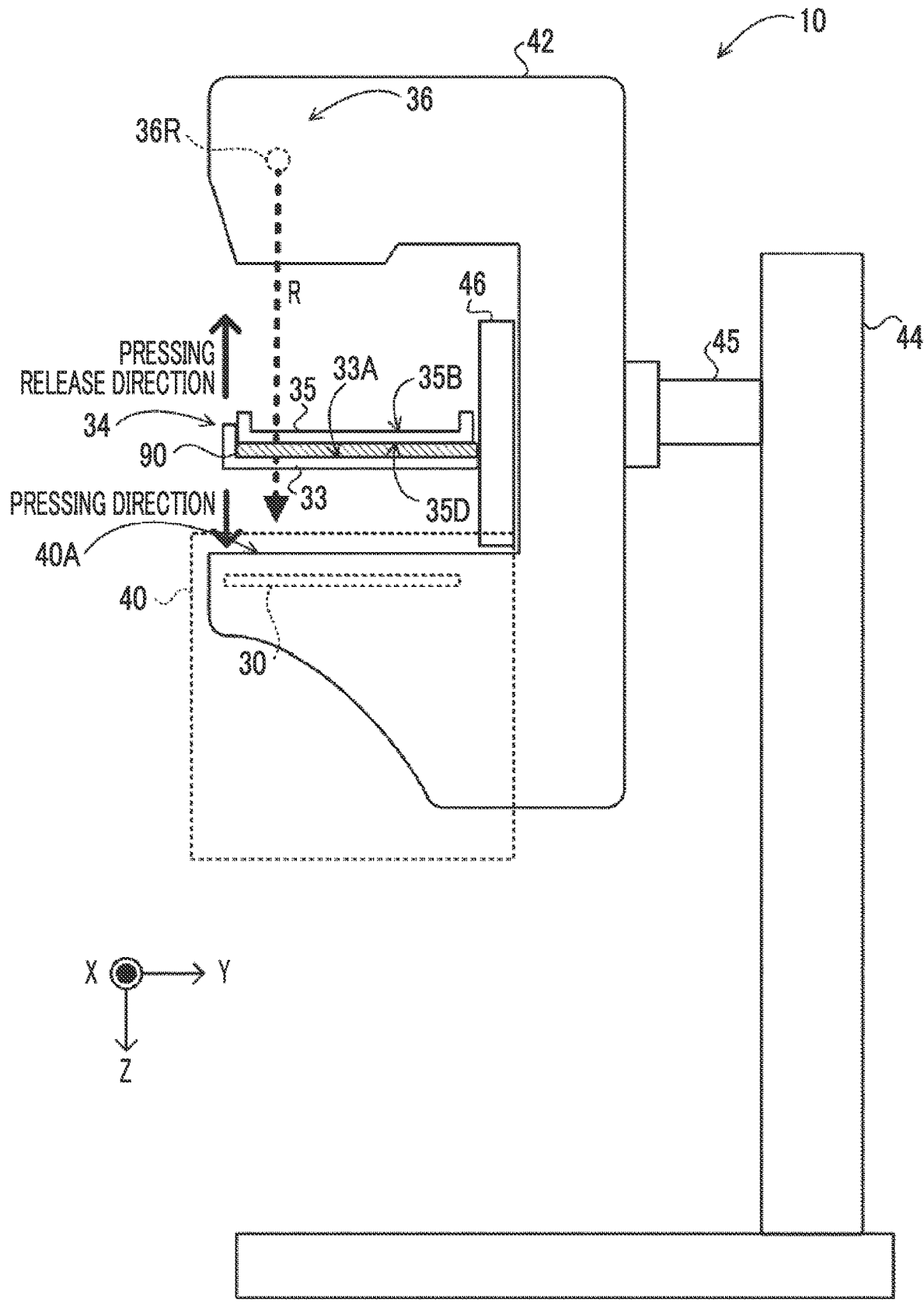
FIG. 3 is a side view illustrating an example of the appearance of the mammography apparatus of the embodiment.

First, the configuration of the radiography system 2 will be described. The radiography system 2 includes a mammography apparatus 10 and a console 12. FIG. 2 is a block diagram illustrating an example of the configuration of the mammography apparatus 10 and the console 12. FIG. 3 is a side view illustrating an example of the appearance of the mammography apparatus 10 of the embodiment.

The mammography apparatus 10 of the embodiment is an apparatus that irradiates the breast of a subject as an object with radiation R (for example, X-rays) to capture a radiographic image of the breast. In addition, the mammography apparatus 10 may be an apparatus that images the breast of the subject not only in a state in which the subject is standing (standing position state) but also in a state in which the subject sits on a chair (including a wheelchair) or the like (sitting position state).

As illustrated in FIG. 2, the mammography apparatus 10 of the embodiment comprises a control unit 20, a storage unit 22, an interface (I/F) unit 24, an operation unit 26, a radiation detector 30, a pressing plate driving unit 32, an imaging member 34, a radiation emitting unit 36, a radiation source driving unit 37, and a load sensor 38. The control unit 20, the storage unit 22, the I/F unit 24, the operation unit 26, the radiation detector 30, the pressing plate driving unit 32, the radiation emitting unit 36, the radiation source driving unit 37, and the load sensor 38 are connected to each other through a bus 39, such as a system bus or a control bus, so as to be able to transmit and receive various kinds of information.

The control unit 20 of the embodiment controls the overall operation of the mammography apparatus 10 under the control of the console 12. The control unit 20 comprises a central processing unit (CPU) 20A, a read only memory (ROM) 20B, and a random access memory (RAM) 20C. For example, various programs including an imaging control processing program 21 which is executed by the CPU 20A and performs control relating to the capture of a radiographic image are stored in the ROM 20B in advance. The RAM 20C temporarily stores various kinds of data.

The radiation detector 30 detects the radiation R transmitted through the breast which is the object. As illustrated in FIG. 3, the radiation detector 30 is provided in an imaging table 40. In the mammography apparatus 10 of the embodiment, in a case in which imaging is performed, the breast of the subject is positioned on an imaging surface 40A of the imaging table 40 by a user such as a doctor or a radiology technician. The imaging surface 40A or the like with which the breast of the subject comes into contact is made of, for example, carbon in terms of the transmittance and intensity of the radiation R.

The radiation detector 30 detects the radiation R transmitted through the breast of the subject and the imaging table 40, generates a radiographic image on the basis of the detected radiation R, and outputs image data indicating the generated radiographic image. The type of the radiation detector 30 of the embodiment is not particularly limited. For example, the radiation detector 30 may be an indirect-conversion-type radiation detector that converts the radiation R into light and converts the converted light into charge, or may be a direct-conversion-type radiation detector that directly converts the radiation R into charge.

For example, the image data of the radiographic image captured by the radiation detector 30 and various other kinds of information are stored in the storage unit 22. Specific examples of the storage unit 22 include a hard disk drive (HDD) and a solid state drive (SSD). The I/F unit 24 performs communication of various kinds of information with the console 12 through wireless communication or wired communication. In the mammography apparatus 10, the image data of the radiographic image captured by the radiation detector 30 is transmitted to the console 12 through the I/F unit 24 by wireless communication or wired communication.

The operation unit 26 is provided as a plurality of switches in, for example, the imaging table 40 of the mammography apparatus 10. In addition, the operation unit 26 may be provided as a touch panel switch or may be provided as a foot switch that is operated by the user's feet.

The radiation emitting unit 36 comprises a radiation source 36R. As illustrated in FIG. 3, the radiation emitting unit 36 is provided in an arm portion 42 together with the imaging table 40 and a pressing unit 46. In addition, as illustrated in FIG. 3, the mammography apparatus 10 of the embodiment comprises the arm portion 42, a base 44, and a shaft portion 45. The arm portion 42 is held by the base 44 so as to be movable in a vertical direction (Z-axis direction). The shaft portion 45 connects the arm portion 42 to the base 44. The radiation source driving unit 37 can relatively rotate the arm portion 42 with respect to the base 44, using the shaft portion 45 as a rotation axis.

In a case in which the mammography apparatus 10 performs tomosynthesis imaging, with the rotation of the arm portion 42, the radiation source 36R of the radiation emitting unit 36 is continuously moved to each of a plurality of irradiation positions with different irradiation angles (projection angles) by the radiation source driving unit 37. At each irradiation position, the radiation R is emitted from the radiation source 36R in response to an instruction from the console 12, and the radiation detector 30 captures a radiographic image. In the embodiment, an aspect in which the radiation emitting unit 36 is moved to move the radiation source 36R to the irradiation position has been described. However, the present disclosure is not limited to the embodiment. For example, an aspect in which the mammography apparatus 10 comprises a plurality of radiation sources 36R corresponding to each irradiation position may be adopted.

In addition, the imaging member 34 of the embodiment comprises a pressing plate 33 and a member 35. The detailed configuration of each of the pressing plate 33 and the member 35 of the imaging member 34, and the detailed relationship of the capture of a radiographic image and an ultrasound image will be described below, and the configuration of the imaging member 34 for the entire mammography apparatus 10 will be described first.

As illustrated in FIG. 3, the pressing plate 33 of the imaging member 34 is provided to the pressing unit 46. Each of the pressing unit 46 and the arm portion 42 can be relatively rotated with respect to the base 44, using the shaft portion 45 as a rotation axis. In the embodiment, gears (not illustrated) are provided in each of the shaft portion 45, the arm portion 42, and the pressing unit 46. The gears are switched between an engaged state and a disengaged state to connect each of the arm portion 42 and the pressing unit 46 to the shaft portion 45. One or both of the arm portion 42 and the pressing unit 46 connected to the shaft portion 45 are rotated integrally with the shaft portion 45.

Figure 4A:
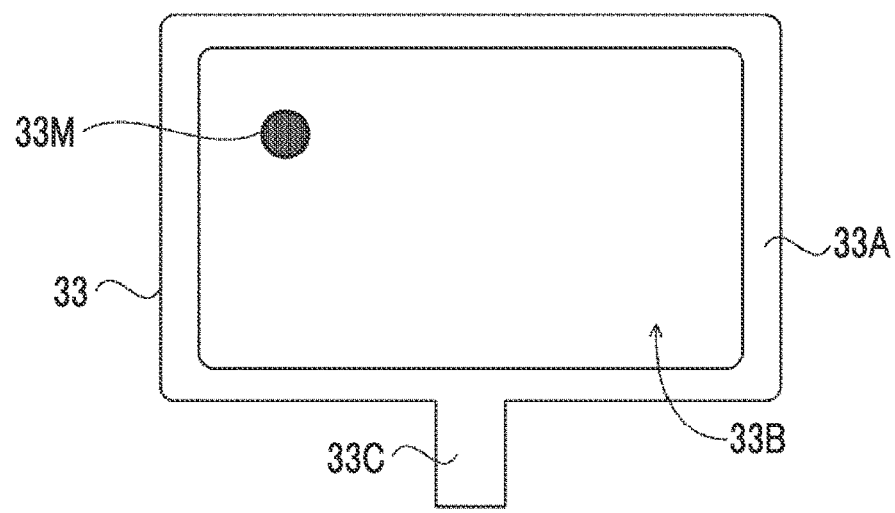
FIG. 4A is a plan view illustrating an example of a state where a pressing plate of an imaging member of the embodiment is seen from a radiation emitting unit side.

As illustrated in FIG. 4A, in the pressing plate 33 of the embodiment, a wall 33A protruding upward (direction toward the radiation emitting unit 36) is provided on the outer peripheral edge of an upper surface 33B as a plate-shaped member. The upper surface 33B is a surface closer to the radiation emitting unit 36, in other words, a surface opposite to the surface that comes into contact with the breast, in the pressing plate 33. As illustrated in FIG. 4A, in a case where the member 35 is provided, a mark 33M which is used for the positioning with the member 35 is provided to the upper surface 33B of the pressing plate 33. The mark 33M is provided at a position where the mark 33M does not overlap the breast image in a case where the radiographic image is captured. FIG. 4A is a plan view illustrating an example of a state where the pressing plate 33 is seen from the radiation emitting unit 36 side. In the embodiment, providing the member 35 to the upper surface 33B of the pressing plate 33 is simply referred to as "providing the member 35 to the pressing plate 33".

The pressing plate 33 has a connection portion 33C, which protrudes outwardly, at a part of the outer periphery, and is connected to the pressing plate driving unit 32 by the connection portion 33C. The pressing plate 33 is moved in the vertical direction (Z-axis direction) by the pressing plate driving unit 32 to press the breast of the subject against the imaging table 40. As illustrated in FIG. 3, for the movement direction of the pressing plate 33, a direction in which the breast is pressed, that is, a direction approaching the imaging surface 40A is referred to as a "pressing direction", and a direction in which the pressing against the breast is released, that is, a direction approaching the radiation emitting unit 36 is referred to as a "pressing release direction". The pressing plate 33 of the embodiment is an example of a pressing member of the present disclosure. Further, the upper surface 33B of the pressing plate 33 is an example of a surface opposite to a surface, with which the breast comes into contact, of the pressing member of the present disclosure.

A connection part where the connection portion 33C of the pressing plate 33 and the pressing plate driving unit 32 are connected is provided with the load sensor 38 such as a load cell for detecting a load applied to the connection part.

Figure 4B:
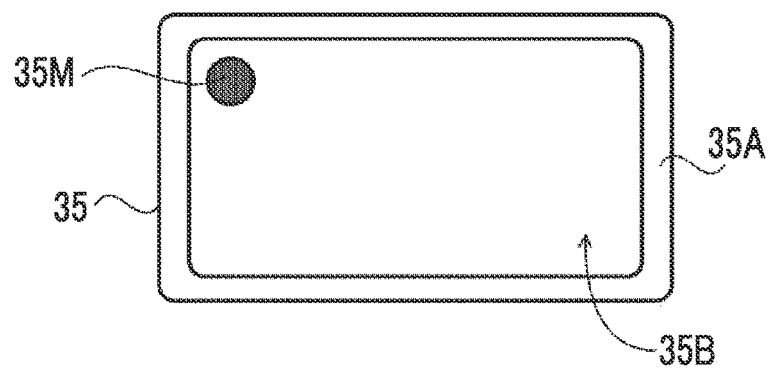
FIG. 4B is a plan view illustrating an example of a state where a member of the imaging member of the embodiment is seen from the radiation emitting unit side.

As illustrated in FIGS. 3 and 4B, in the member 35 of the embodiment, a wall 35A protruding upward (direction toward the radiation emitting unit 36) is provided on the outer peripheral edge of an upper surface 35B as a plate-shaped member. As described below, an acoustic matching member 92 provided on the upper surface 35B of the member 35 has high fluidity. Therefore, the wall 35A is provided on the upper surface 35B and the acoustic matching member 92 is provided to be surrounded by the wall 35A so that it is possible to suppress the flowing of the acoustic matching member 92 toward the pressing plate 33 or a coupling material 90. As illustrated in FIG. 4B, in the member 35 of the embodiment, an aspect in which the wall 35A is provided to the entire periphery of the upper surface 35B is illustrated, but the position where the wall 35A is provided is not limited to the embodiment. For example, in a case where the upper surface 35B has a rectangular shape, an aspect in which the wall 35A is provided at least a side corresponding to the chest wall side of the subject and a pair of facing sides intersecting the side corresponding to the chest wall side may be adopted. Further, the wall 35A may be provided according to the movement direction or the like of the ultrasound probe 65.

The upper surface 35B is a surface closer to the radiation emitting unit 36, in other words, a surface facing the radiation emitting unit 36 via the acoustic matching member 92. As illustrated in FIG. 4B, in a case where the member 35 is provided on the upper surface 33B of the pressing plate 33, a mark 35M which is used for the positioning with the pressing plate 33 is provided to the upper surface 35B of the member 35. FIG. 4B is a plan view illustrating an example of a state where the member 35 is seen from the radiation emitting unit 36 side. The member 35 of the embodiment is an example of an ultrasonography member of the present disclosure.

Figure 4C:
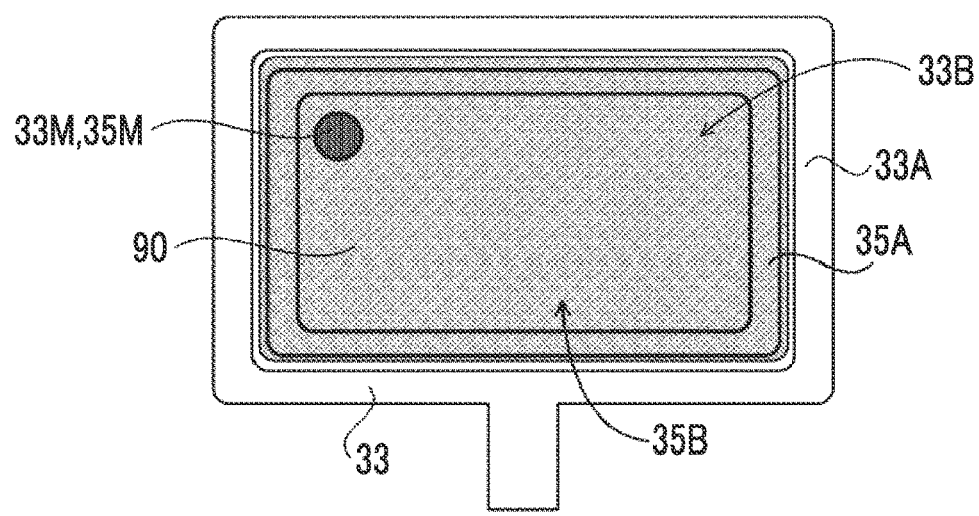
FIG. 4C is a plan view illustrating an example of a state where the member is provided on the pressing plate in the imaging member of the embodiment.

The member 35 is provided in a state where a lower surface 35D, which is opposite to the upper surface 35B, faces the upper surface 33B of the pressing plate 33 via the coupling material 90. Specifically, as illustrated in FIG. 4C, the member 35 is provided on the upper surface 33B of the pressing plate 33 via the coupling material 90 in a state where the mark 33M of the pressing plate 33 matches the mark 35M of the member 35. The upper surface 35B of the member 35 is an example of a first surface of the ultrasonography member of the present disclosure, and the lower surface 35D is an example of a second surface of the ultrasonography member of the present disclosure.

Figure 4D:
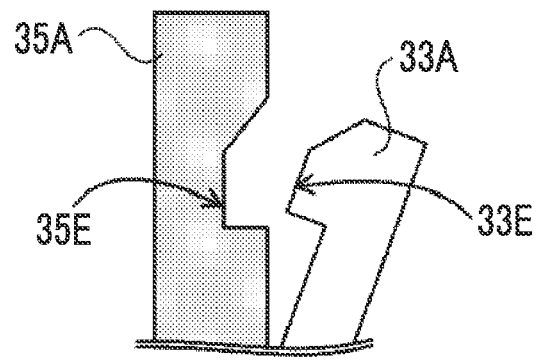
FIG. 4D is a diagram describing an example of fixation between the pressing plate and the member.
Figure 4E:
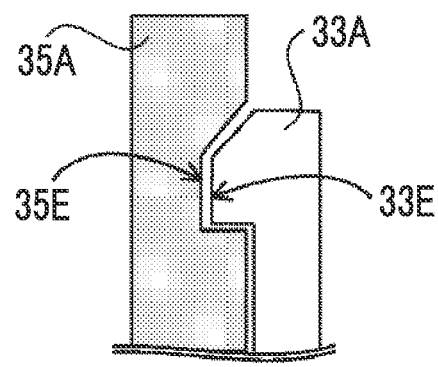
FIG. 4E is a diagram describing an example of fixation between the pressing plate and the member.

As an example, in the embodiment, a convex fixing portion 33E is provided on the wall 33A of the pressing plate 33 and a concave fixing portion 35E is provided on the wall 35A of the member 35 as illustrated in FIGS. 4D and 4E. The member 35 is fixed to the pressing plate 33 by fitting the fixing portion 33E of the pressing plate 33 into the upper surface 35B of the member 35 such that the fixing portion 33E is in a state illustrated in FIG. 4E from a state illustrated in FIG. 4D. The fixing portion 33E and the fixing portion 35E may not be provided on the entirety of the wall 33A and the wall 35A, respectively, and for example, may be provided only on the wall 33A and the wall 35A respectively corresponding to a partial side of the pressing plate 33 and the member 35.

Figure 4F:
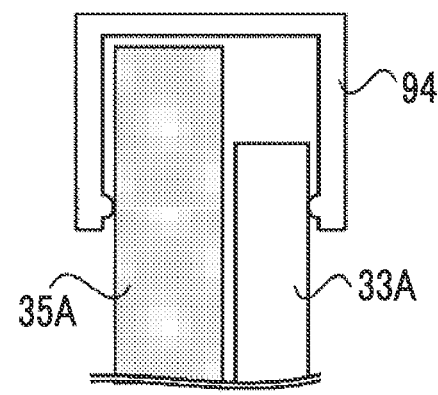
FIG. 4F is a diagram describing another example of fixation between the pressing plate and the member.

In the embodiment, an aspect in which the member 35 is fixed to the pressing plate 33 by the fixing portion 33E and the fixing portion 35E respectively provided to the pressing plate 33 and the member 35 is described, but the fixing method is not limited to the embodiment. For example, an aspect in which the member 35 is fixed to the pressing plate 33 by a separately provided fixture may be adopted. In the example illustrated in FIG. 4F, the member 35 is fixed to the pressing plate 33 by sandwiching all or a part of each of the distal end portion of the wall 33A of the pressing plate 33 and the distal end portion of the wall 35A of the member 35 using a fixture 94.

As illustrated in FIGS. 3 and 4C, in the imaging member 34 of the embodiment, the member 35 is provided to be surrounded by the wall 33A of the upper surface 33B of the pressing plate 33. Accordingly, the size of the upper surface 35B of the member 35 is smaller than the size of the upper surface 33B of the pressing plate 33.

It is preferable that the pressing plate 33 and the member 35 are optically transparent in order to check the positioning or the pressed state in the pressing of the breast. In addition, the pressing plate 33 is made of a material having high transmittance for the radiation R. It is desirable that the pressing plate 33 and the member 35 are made of a material that facilitates the transmission of ultrasonic waves from the ultrasound probe 65 (refer to FIG. 7, which will be described in detail below) of the ultrasonography apparatus 16. Examples of the material forming the pressing plate 33 and the member 35 include resins such as polymethylpentene, silicone rubber, polycarbonate, acrylic, and polyethylene terephthalate. In particular, polymethylpentene and silicone rubber are suitable as the material forming the pressing plate 33 and the member 35 since polymethylpentene and silicone rubber have low rigidity, high elasticity, and high flexibility, are similar to living tissue (breast tissue), and have suitable values for acoustic impedance that affects the reflectance of ultrasonic waves and an attenuation coefficient that affects the attenuation of ultrasonic waves. The member constituting the pressing plate 33 and the member 35 are not limited to the embodiment. For example, the member constituting the pressing plate 33 may be a film-like member.

The imaging member 34 is not limited to an imaging member that presses the entire breast, and the imaging member 34 may be an imaging member that presses a part of the breast. In other words, the imaging member 34 may be smaller than the breast. For example, a pressing plate used in so-called spot imaging which captures a radiographic image of only a region where a lesion is present is known as the pressing plate 33 of the imaging member 34.

Figure 5:
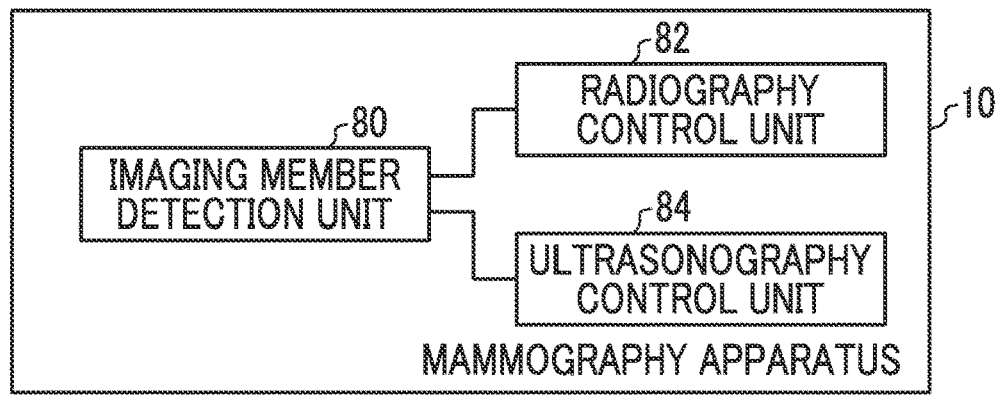
FIG. 5 is a functional block diagram illustrating an example of the function of the mammography apparatus of the embodiment.

FIG. 5 is a functional block diagram illustrating an example of the configuration of the mammography apparatus 10 according to this embodiment. As illustrated in FIG. 5, the mammography apparatus 10 of the embodiment comprises an imaging member detection unit 80, a radiography control unit 82, and an ultrasonography control unit 84. As an example, in the mammography apparatus 10 of the embodiment, the CPU 20A executes the imaging control processing program 21 stored in the ROM 20B so that the control unit 20 functions as the imaging member detection unit 80, the radiography control unit 82, and the ultrasonography control unit 84. The imaging control processing program 21 of the embodiment is an example of a control program of the present disclosure.

The imaging member detection unit 80 detects whether the member 35 is provided to the pressing plate 33 on the basis of the detection result of the load sensor 38, and outputs the detection result to the radiography control unit 82 and the ultrasonography control unit 84. Further, the imaging member detection unit 80 detects whether the coupling material 90 is provided between the pressing plate 33 and the member 35 on the basis of the detection result of the load sensor 38, and outputs the detection result to the ultrasonography control unit 84.

As an example, the imaging member detection unit 80 of the embodiment determines that the coupling material 90 is provided to the pressing plate 33 in a case where a load within a predetermined range from a first threshold value is applied to the pressing plate 33 on the basis of the detection result of the load sensor 38. The first threshold value in this case is determined on the basis of, for example, the weight of the coupling material 90. Further, the imaging member detection unit 80 determines that the member 35 is provided without providing the coupling material 90 to the pressing plate 33 in a case where a load out of the predetermined range from the first threshold value is applied to the pressing plate 33.

Furthermore, the imaging member detection unit 80 determines that the member 35 is provided to the pressing plate 33 via the coupling material 90 in a case where a load within a predetermined range from a second threshold value is further applied to the pressing plate 33 on the basis of the detection result of the load sensor 38. The second threshold value in this case is determined on the basis of, for example, the weight of the coupling material 90 and the member 35.

A method for the imaging member detection unit 80 to detect whether the member 35 is provided on the upper surface 33B of the pressing plate 33, and a method for the imaging member detection unit 80 to detect whether the coupling material 90 is provided between the pressing plate 33 and the member 35 are not limited to the methods described in the embodiment. For example, an aspect in which a sensor detecting light such as visible light is provided to the imaging table 40 and the providing of the member 35 and the coupling material 90 is detected in a case where the sensor detects that the light is blocked by the member 35 may be adopted. For example, an aspect in which whether the member 35 and the coupling material 90 are provided is determined on the basis of a captured image obtained by imaging the imaging member 34 by an imaging device provided outside the mammography apparatus 10 may be adopted. Further, for example, since the electrical resistance value of the entire imaging member 34 is changed in a case where the coupling material 90 and the member 35 are provided, an aspect in which whether the member 35 and the coupling material 90 are provided is determined by observing the change in current value flowing in the imaging member 34 may be adopted.

Figure 6A:
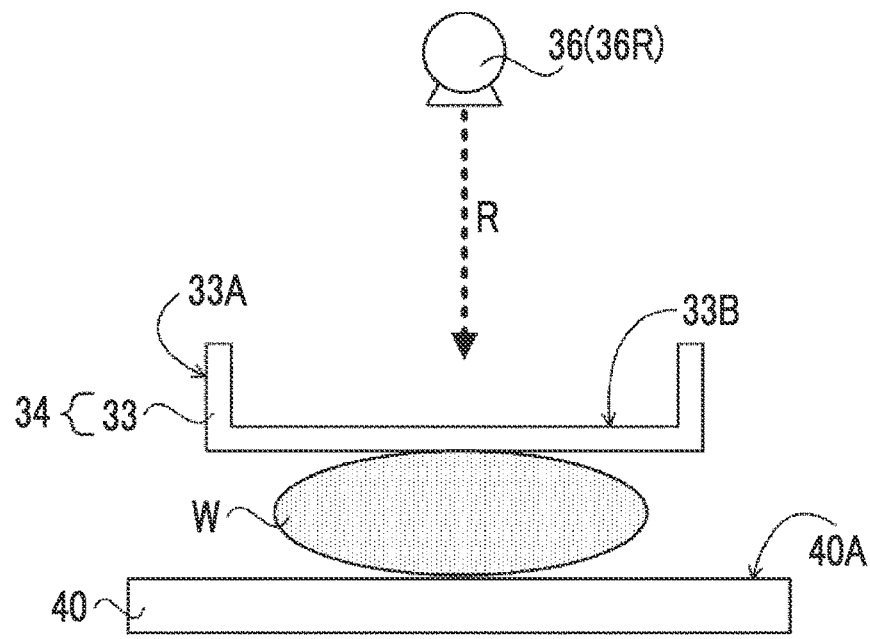
FIG. 6A is a sectional view illustrating an example of a state of the imaging member in a state where a radiographic image is captured by the mammography apparatus in a radiography system of the embodiment.

The radiography control unit 82 performs control of irradiating the breast, which is in the pressed state by the pressing plate 33 of the imaging member 34, with the radiation R and causing the radiation detector 30 to capture a radiographic image of the breast. FIG. 6A is a sectional view illustrating an example of a state of the imaging member 34 in a state where a radiographic image is captured by the mammography apparatus 10 in the radiography system 2 of the embodiment. In the embodiment, as illustrated in FIG. 6A, in case of capturing a radiographic image, a breast W which is positioned on the imaging surface 40A of the imaging table 40 of the mammography apparatus 10 is fixed by being pressed by the pressing plate 33. The radiography control unit 82 irradiates the breast W in the pressed state with the radiation R from the upper surface 33B side of the pressing plate 33 using the radiation source 36R of the radiation emitting unit 36 to generate a radiographic image by the radiation detector 30.

In a case where a radiographic image is captured in a state where at least one of the coupling material 90 or the member 35 is provided on the pressing plate 33, at least one of the coupling material 90 or the member 35 provided on the pressing plate 33 may affect the capture radiographic image in some cases. Thus, in the embodiment, as illustrated in FIG. 6A, a radiographic image is captured in a state where the acoustic matching member 92 is not provided on the pressing plate 33 and also the coupling material 90 is not provided on the pressing plate 33. Therefore, the radiography control unit 82 performs control of prohibiting the capture of a radiographic image in a case where the member 35 is provided on the upper surface 33B of the pressing plate 33 on the basis of the detection result of the imaging member detection unit 80. Further, the radiography control unit 82 performs control of warning against the capture of a radiographic image in a case where the member 35 is provided on the upper surface 33B of the pressing plate 33 on the basis of the detection result of the imaging member detection unit 80.

Figure 6B:
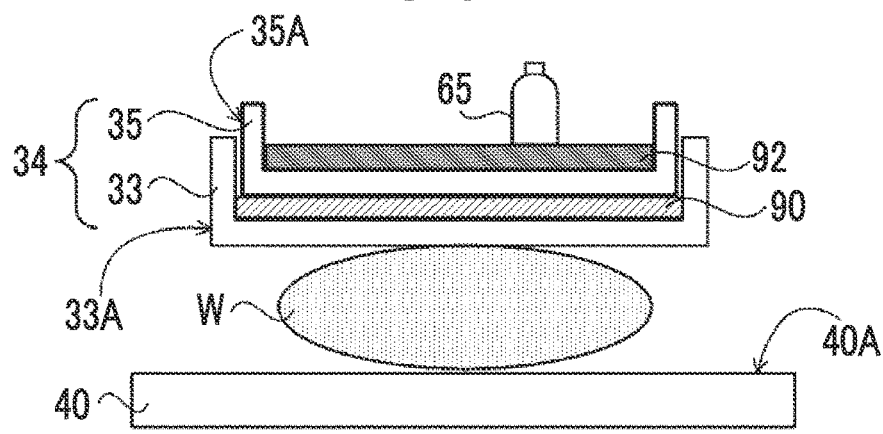
FIG. 6B is a sectional view illustrating an example of a state of the imaging member in a state where an ultrasound image is captured by an ultrasonography apparatus in the radiography system of the embodiment.

The ultrasonography control unit 84 performs control of causing the ultrasonography apparatus 16 to capture an ultrasound image of the breast in a state where the member 35 is provided on the upper surface 33B of the pressing plate 33 via the coupling material 90 having lower fluidity than the acoustic matching member 92 and the acoustic matching member 92 is provided on the upper surface 35B of the member 35. FIG. 6B is a sectional view illustrating an example of a state of the imaging member 34 in a state where an ultrasound image is captured by the ultrasonography apparatus 16 in the radiography system 2 of the embodiment. In the embodiment, as illustrated in FIG. 6B, an ultrasound image is captured while the breast W on the imaging surface 40A of the imaging table 40 of the mammography apparatus 10 is in the pressed state by the pressing plate 33. Further, in the embodiment, an ultrasound image is captured by scanning the upper surface 35B using the ultrasound probe 65 in a state where the member 35 is provided on the upper surface 33B of the pressing plate 33 via the coupling material 90 and the acoustic matching member 92 such as echo jelly is provided on the upper surface 35B of the member 35.

In a case where an air layer is included between the pressing plate 33 and the member 35, since the air layer is difficult to transmit the ultrasonic waves, the image quality of the ultrasound image of the breast W at the position corresponding to the air layer may be degraded or imaging may not be performed in some cases. Thus, in the embodiment, the adhesion between the pressing plate 33 and the member 35 is improved by providing the coupling material 90 having relatively high flexibility between the pressing plate 33 and the member 35. Even in a case where scanning is performed using the ultrasound probe 65 or a case where the pressing plate 33 and the member 35 are bent by the breast being in the pressed state, the bending is absorbed by the coupling material 90, and thus it is possible to suppress the entering of the air layer or the like between the pressing plate 33 and the member 35. Even in a case where air enters between the pressing plate 33 and the member 35, it is possible to discharge the entered air by the coupling material 90 being bent.

As the coupling material 90 of the embodiment, a member having low attenuation of ultrasonic waves, in other words, a member having high penetration and having acoustic characteristics close to the acoustic impedance of breast tissue is used.

By using such a member is used as the coupling material 90, it is possible to suppress an influence on an ultrasound image captured in a state where the coupling material 90 is provided.

Further, as the coupling material 90 of the embodiment, a member that has lower fluidity than the acoustic matching member 92 and is relatively easily removed from the upper surface 33B of the pressing plate 33 is used.

As the coupling material 90 described above, a sheet-like member using oil gel is exemplified.

The thickness of each of the coupling material 90 and the member 35 is preferably thinner from the viewpoint of increasing the penetration, and the specific thickness may be determined according to a member or the like of the coupling material 90 and the member 35.

On the other hand, as the acoustic matching member 92, a member having relatively high fluidity is used in order to improve the scanning performance of the ultrasound probe 65, and a member having higher fluidity than at least the coupling material 90 is used. As the acoustic matching member 92 described above, lubricating gel such as so-called echo jelly is exemplified.

The ultrasonography control unit 84 performs control of prohibiting the capture of an ultrasound image in a case where the member 35 is not provided on the upper surface 33B of the pressing plate 33 on the basis of the detection result of the imaging member detection unit 80. Further, the ultrasonography control unit 84 performs control of warning against the capture of an ultrasound image in a case where the member 35 is not provided on the upper surface 33B of the pressing plate 33 on the basis of the detection result of the imaging member detection unit 80. Furthermore, the ultrasonography control unit 84 performs control of prohibiting the capture of an ultrasound image in a case where the coupling material 90 is not provided between the upper surface 33B of the pressing plate 33 and the lower surface 35D of the member 35 on the basis of the detection result of the imaging member detection unit 80.

The console 12 of the embodiment has a function of controlling the mammography apparatus 10 using, for example, an imaging order and various kinds of information acquired from a radiology information system (RIS) 5 through a wireless communication local area network (LAN) and an instruction or the like input by the user through an operation unit 56.

The console 12 of the embodiment is a server computer, for example. As illustrated in FIG. 2, the console 12 comprises a control unit 50, a storage unit 52, an I/F unit 54, the operation unit 56, and a display unit 58. The control unit 50, the storage unit 52, the I/F unit 54, the operation unit 56, and the display unit 58 are connected to each other through a bus 59, such as a system bus or a control bus, so as to be able to transmit and receive various kinds of information.

The control unit 50 of the embodiment controls the overall operation of the console 12. The control unit 50 comprises a CPU 50A, a ROM 50B, and a RAM 50C. Various programs including a control processing program 51, which will be described below, executed by the CPU 50A are stored in the ROM 50B in advance. The RAM 50C temporarily stores various kinds of data. The image data of the radiographic image captured by the mammography apparatus 10 and various other kinds of information are stored in the storage unit 52.

The operation unit 56 is used by the user to input, for example, various kinds of information or instructions relating to the capture of a radiographic image and including an instruction to emit the radiation R. Therefore, the operation unit 56 of the embodiment includes at least an irradiation instruction button that is pressed by the user to input an instruction to emit the radiation R. The operation unit 56 is not particularly limited. Examples of the operation unit 56 include various switches, a touch panel, a touch pen, and a mouse. The display unit 58 displays various kinds of information. In addition, the operation unit 56 and the display unit 58 may be integrated into a touch panel display.

The I/F unit 54 performs communication of various kinds of information between the mammography apparatus 10, the RIS 5, and the image preservation system 18 using wireless communication or wired communication. In the radiography system 2 of the embodiment, the console 12 receives the image data of the radiographic image captured by the mammography apparatus 10 from the mammography apparatus 10 through the I/F unit 54, using wireless communication or wired communication.

Figure 7:
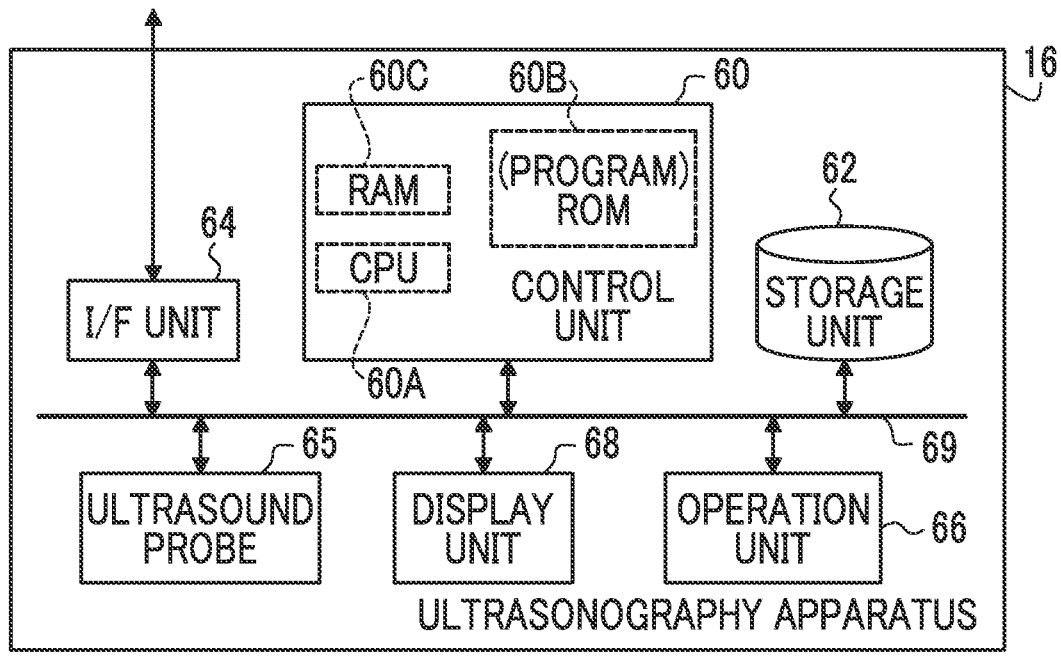
FIG. 7 is a block diagram illustrating an example of the configuration of an ultrasonography apparatus of the embodiment.

Next, the configuration of the ultrasonography apparatus 16 will be described. FIG. 7 is a block diagram illustrating an example of the configuration of the ultrasonography apparatus 16. The ultrasonography apparatus 16 is an apparatus used by the user to capture an ultrasound image of the breast of the subject as the object and is a so-called handheld ultrasonography apparatus.

As illustrated in FIG. 7, the ultrasonography apparatus 16 comprises a control unit 60, a storage unit 62, an I/F unit 64, the ultrasound probe 65, an operation unit 66, and a display unit 68. The control unit 60, the storage unit 62, the I/F unit 64, the ultrasound probe 65, the operation unit 66, and the display unit 68 are connected to each other through a bus 69, such as a system bus or a control bus, so as to be able to transmit and receive various kinds of information.

The control unit 60 of the embodiment controls the overall operation of the ultrasonography apparatus 16. The control unit 60 comprises a CPU 60A, a ROM 60B, and a RAM 60C. Various programs executed by the CPU 60A are stored in the ROM 60B in advance. The RAM 60C temporarily stores various kinds of data.

The image data of the captured ultrasound image and various other kinds of information are stored in the storage unit 62. Specific examples of the storage unit 62 include an HDD, an SSD, and the like.

The ultrasound probe 65 is moved along the upper surface 35B (refer to FIG. 3, a surface opposite to the surface that comes into contact with the breast of the subject) of the member 35 by the user and scans the breast with ultrasonic waves to acquire an ultrasound image of the breast. Specifically, in a case in which ultrasonography is performed, the ultrasound probe 65 is moved by the user along the upper surface 35B of the member 35 in a state in which the acoustic matching member 92 such as echo jelly is applied onto the upper surface 35B of the member 35.

The ultrasound probe 65 comprises a plurality of ultrasound transducers (not illustrated) which are one-dimensionally or two-dimensionally arranged. Each of the ultrasound transducers transmits ultrasonic waves on the basis of an applied drive signal, receives ultrasound echoes, and outputs a received signal.

For example, each of the plurality of ultrasound transducers is a transducer configured by forming electrodes at both ends of a piezoelectric material (piezoelectric body), such as a piezoelectric ceramic typified by lead (Pb) zirconate titanate (PZT) or a polymeric piezoelectric element typified by polyvinylidene difluoride (PVDF). In a case in which a pulsed or continuous wave drive signal is transmitted to apply a voltage to the electrodes of the transducer, the piezoelectric body is expanded and contracted. Pulsed or continuous ultrasonic waves are generated from each transducer by the expansion and contraction and the ultrasonic waves are combined to form an ultrasound beam. Each transducer receives the propagated ultrasonic waves and is then expanded and contracted to generate an electrical signal. The electrical signal is output as an ultrasound received signal and is input to the main body (not illustrated) of the ultrasonography apparatus 16 through a cable (not illustrated).

The operation unit 66 is used by the user to input, for example, various kinds of information or instructions relating to the capture of an ultrasound image. The operation unit 66 is not particularly limited. Examples of the operation unit 66 include various switches, a touch panel, a touch pen, and a mouse. The display unit 68 displays, for example, various kinds of information or an ultrasound image corresponding to the received signal from the ultrasound probe 65. In addition, the operation unit 66 and the display unit 68 may be integrated into a touch panel display.

The I/F unit 64 performs communication of various kinds of information between the RIS 5 and the image preservation system 18 using wireless communication or wired communication. The image data of the ultrasound image captured by the ultrasonography apparatus 16 is transmitted to the image preservation system 18 through the I/F unit 64 by wireless communication or wired communication.

Figure 8:
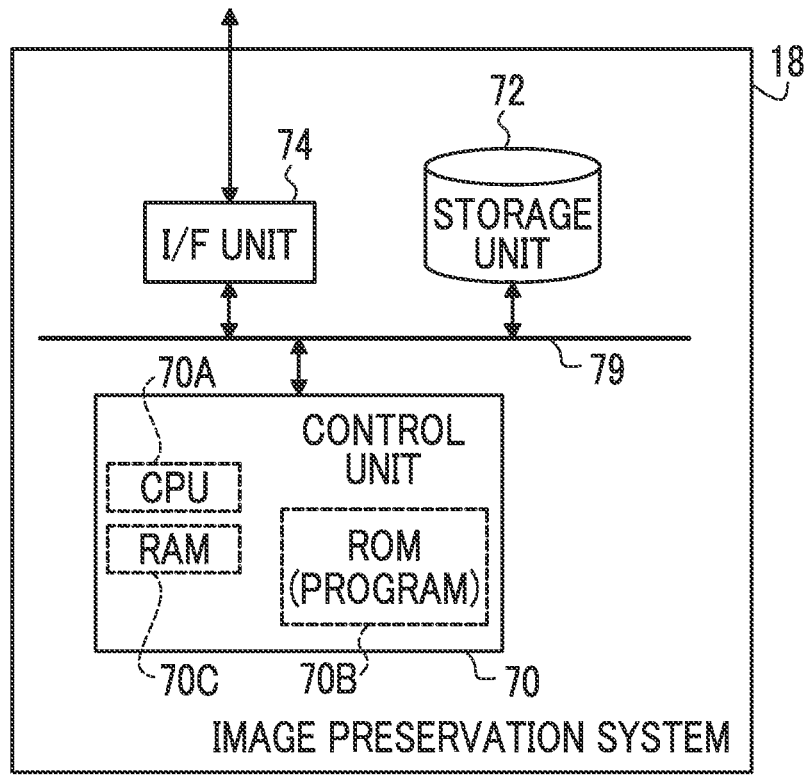
FIG. 8 is a block diagram illustrating an example of the configuration of an image preservation system of the embodiment.

Next, the configuration of the image preservation system 18 will be described. FIG. 8 is a block diagram illustrating an example of the configuration of the image preservation system 18. The image preservation system 18 is a system that preserves the image data of the radiographic image captured by the radiography system 2 and the image data of the ultrasound image captured by the ultrasonography apparatus 16. The image preservation system 18 extracts an image corresponding to a request from, for example, the console 12, the ultrasonography apparatus 16, and other reading devices (not illustrated) from the preserved radiographic images and ultrasound images, and transmits the extracted image to the apparatus which is the request source. A specific example of the image preservation system 18 is picture archiving and communication systems (PACS).

As illustrated in FIG. 8, the image preservation system 18 comprises a control unit 70, a storage unit 72, and an I/F unit 74. The control unit 70, the storage unit 72, and the I/F unit 74 are connected to each other through a bus 79, such as a system bus or a control bus, so as to be able to transmit and receive various kinds of information.

The control unit 70 of the embodiment controls the overall operation of the image preservation system 18. The control unit 70 comprises a CPU 70A, a ROM 70B, and a RAM 70C. Various programs executed by the CPU 70A are stored in the ROM 70B in advance. The RAM 70C temporarily stores various kinds of data.

The storage unit 72 is a so-called database that stores each of the image data of the radiographic image and the image data of the ultrasound image in an association manner with, for example, an imaging order or information relating to the subject.

The I/F unit 74 has a function of performing communication of various kinds of information with the console 12 and the ultrasonography apparatus 16 using wireless communication or wired communication.

Next, the operation of the medical imaging system 1 of the embodiment will be described with reference to the drawings.

Figure 9:
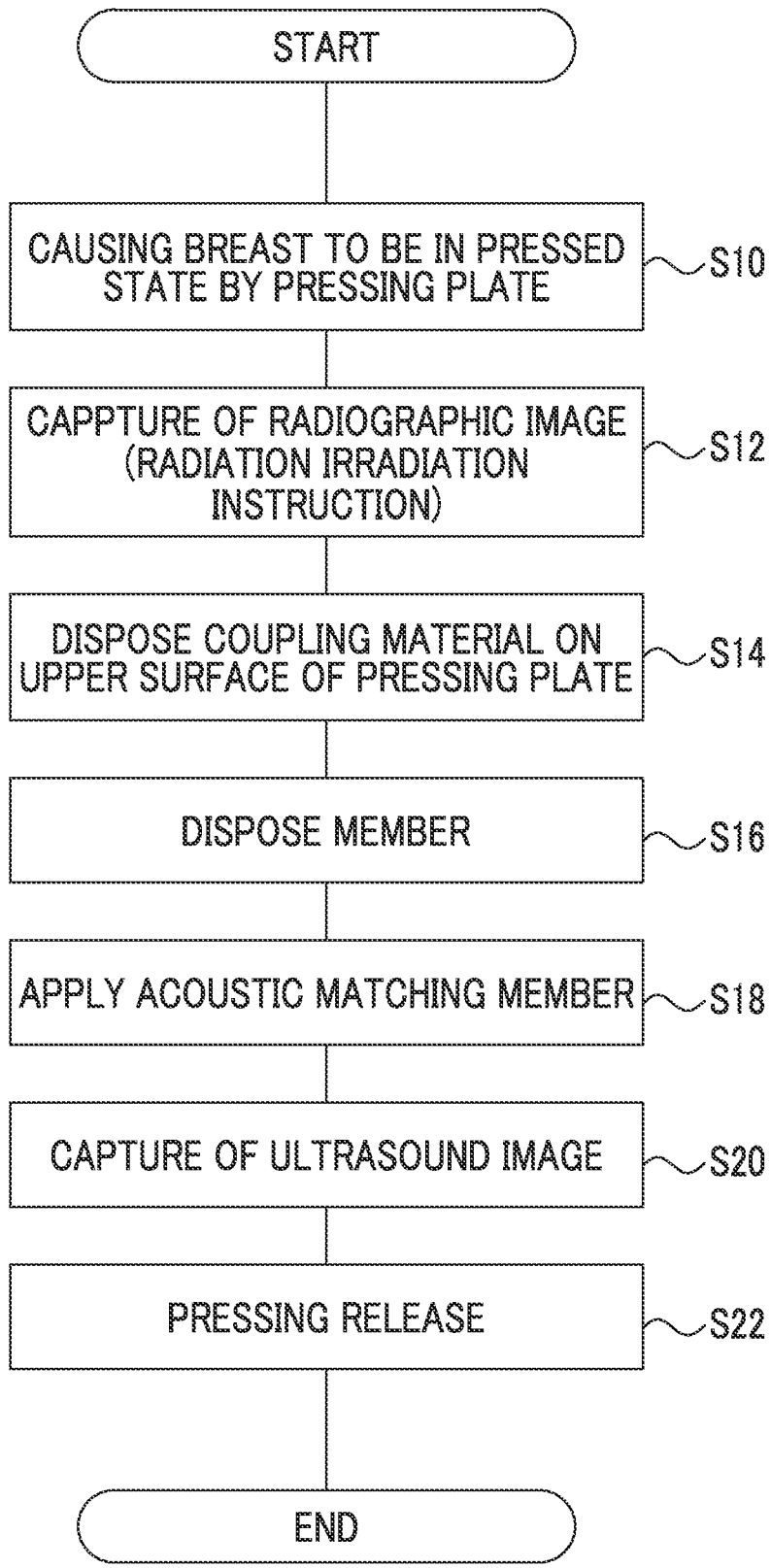
FIG. 9 is a flowchart illustrating an example of the flow of a case where a radiographic image and an ultrasound image are captured in the medical imaging system of the embodiment.

First, the basic flow of a case where a radiographic image and an ultrasound image are captured in the medical imaging system 1 of the embodiment will be described. FIG. 9 is a flowchart illustrating an example of the flow of a case where a radiographic image and an ultrasound image are captured in the medical imaging system 1 of the embodiment. As an example, in the medical imaging system 1 of the embodiment, in a case where both a radiographic image and an ultrasound image are captured, a radiographic image is captured first.

First, in step S10 of FIG. 9, the user causes the breast to be in a pressed state by moving the pressing plate 33 in the pressing direction. In a case in which the mammography apparatus 10 of the embodiment captures a radiographic image, first, the user positions the breast of the subject on the imaging surface 40A of the imaging table 40 of the mammography apparatus 10. In a case in which the positioning is completed, the user inputs a pressing instruction through the operation unit 26 of the mammography apparatus 10.

The pressing of the breast by the pressing plate 33 makes it possible to develop the overlap between the mammary gland tissues and to easily determine whether a lesion is a benign lesion or a malignant lesion. In addition, since the breast is fixed to the imaging table 40 by being pressed by the pressing plate 33, the body movement of the subject is suppressed, and therefore, it is possible to suppress the blurring of a radiographic image caused by the body movement. Further, since the breast is pressed by the pressing plate 33, the thickness of the breast is reduced, and therefore, it is possible to reduce the amount of radiation emitted to the breast.

As an example, in the mammography apparatus 10 of the embodiment, in a case where the fixing of the breast by the pressing plate 33 is completed, the user inputs information indicating that the pressing is completed, through the operation unit 26 of the mammography apparatus 10 or the operation unit 56 of the console 12.

In step S12, the user inputs an instruction to capture a radiographic image. As an example, in the embodiment, the radiation detector 30 functions according to the irradiation instruction to emit radiation R, which is input by the user pressing the irradiation instruction button included in the operation unit 56 of the console 12, as the imaging instruction, and the image data indicating the radiographic image of the breast captured by the radiation detector 30 is output from the mammography apparatus 10 to the console 12.

In a case where the capture of a radiographic image is ended, in step S14, the user disposes the coupling material 90 on the upper surface 33B of the pressing plate 33 as described above. In step S16, the user disposes the member 35 on the coupling material 90. As described above, in the embodiment, since the member 35 is appropriately disposed by providing the member 35 such that the mark 33M of the pressing plate 33 and the mark 35M of the member 35 overlap each other, it is possible to quickly dispose the member 35.

In step S18, the user applies the acoustic matching member 92 on the upper surface 35B of the member 35. By switching the order of step S16 and step S18, the member 35 on which the acoustic matching member 92 has been applied may be provided on the pressing plate 33. In this case, the acoustic matching member 92 can be easily provided regardless of the position of the member 35.

In step S20, the user scans the upper surface 35B of the member 35 using the ultrasound probe 65 of the ultrasonography apparatus 16 to capture the ultrasound image of the breast.

In a case where the capture of an ultrasound image is ended, in step S22, the user releases the pressing of the breast by moving the imaging member 34 (pressing plate 33 and member 35) in the pressing release direction to end a series of the present imaging. After the pressing of the breast of the subject is released, the user detaches the member 35 from the pressing plate 33, and removes the acoustic matching member 92 from the upper surface 35B of the member 35.

Next, the operation of the mammography apparatus 10 of the embodiment will be described with reference to the drawings.

Figure 10:
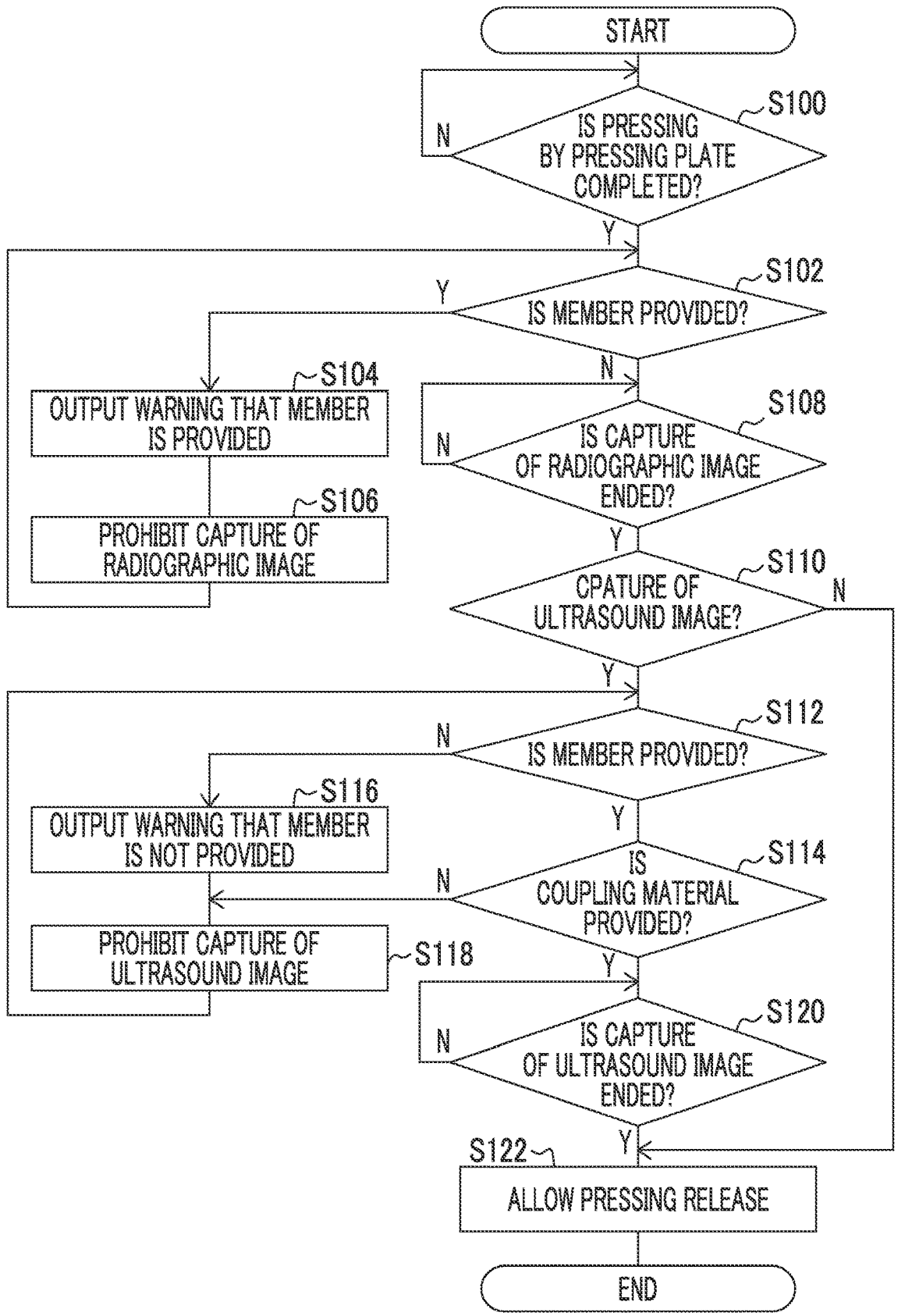
FIG. 10 is a flowchart illustrating an example of the flow of an imaging control process in the mammography apparatus of the embodiment.

For example, in a case in which the mammography apparatus 10 of the embodiment receives an imaging order and an imaging start instruction from the console 12, the CPU 20A of the control unit 20 executes the imaging control processing program 21 stored in the ROM 20B to execute the imaging control process of which an example is illustrated in FIG. 10. FIG. 10 is a flowchart illustrating an example of the flow of the imaging control process of the mammography apparatus 10 of the embodiment.

In step S100 of FIG. 10, the radiography control unit 82 determines whether the pressing of the breast by the pressing plate 33 is completed. As described above, until the user inputs information indicating that the pressing is completed, the determination of step S100 is negative. On the other hand, in a case where the user inputs the information indicating that the pressing is completed, the determination of step S100 is affirmative, and the process proceeds to step S102.

In step S102, the radiography control unit 82 determines whether the member 35 is provided on the upper surface 33B of the pressing plate 33 on the basis of the detection result of the imaging member detection unit 80 as described above. In a case where the member 35 is provided on the upper surface 33B of the pressing plate 33, the determination of step S102 is affirmative, and the process proceeds to step S104.

In step S104, the radiography control unit 82 outputs a warning regarding that the member 35 is provided on the upper surface 33B of the pressing plate 33. The method for the radiography control unit 82 to warn of the member 35 being provided is not particularly limited. However, for example, an aspect in which characters indicating the warning are displayed on the display unit 58 of the console 12 or sound indicating the warning is output from the display unit 58 in a case where the display unit 58 includes a speaker or the like may be adopted. For example, an aspect in which a warning that the disposition of the member 35 is prohibited is output may be adopted.

In step S106, the radiography control unit 82 performs control of prohibiting the capture of a radiographic image, and the process returns to step S102. As an example, in a case where the user inputs an instruction to emit radiation, through the operation unit 56, the radiography control unit 82 of the embodiment causes the display unit 58 of the console 12 to display an error message and does not receive an irradiation instruction to prohibit the capture of a radiographic image.

On the other hand, in a case where the member 35 is not provided on the upper surface 33B of the pressing plate 33, the determination of step S102 is negative, and the process proceeds to step S108.

In step S108, the radiography control unit 82 determines whether the capture of a radiographic image is ended. For example, in a case in which the image data indicating the radiographic image captured by the radiation detector 30 is transmitted to the console 12, the radiography control unit 82 of the embodiment determines that the capture of a radiographic image is ended. A method for determining whether the capture of a radiographic image is ended is not limited to the embodiment. For example, an aspect in which an instruction to end the capture of a radiographic image which is input through the operation unit 56 of the console 12 is received may be adopted. Until the capture of a radiographic image is ended, the determination of step S108 is negative. On the other hand, in a case where the capture of a radiographic image is ended, the determination of step S108 is affirmative, and the process proceeds to step S110.

In step S110, the ultrasonography control unit 84 determines whether to capture an ultrasound image. As an example, in a case where an instruction to capture both a radiographic image and an ultrasound image is included in the imaging order or the user inputs an instruction to capture an ultrasound image through the operation unit 56, the ultrasonography control unit 84 of the embodiment determines to capture an ultrasound image. In a case in which an ultrasound image is not captured, the determination of step S110 is negative, and the process proceeds to step S122. On the other hand, in a case where an ultrasound image is captured, the determination of step S110 is affirmative, and the process proceeds to step S112.

As aspect in which in a case where an ultrasound image has not been captured yet after a radiographic image is captured, the user inputs an instruction indicating whether to release the pressing of the breast by the imaging member 34, through the operation unit 56 may be adopted. In this aspect, until the user inputs an instruction to release the pressing of the breast by the imaging member 34, it is regarded that there is a possibility of capturing an ultrasound image, and the pressed state of the breast by the imaging member 34 can be maintained.

In step S112, the ultrasonography control unit 84 determines whether the member 35 is provided on the upper surface 33B of the pressing plate 33 on the basis of the detection result of the imaging member detection unit 80 as described above. In a case where the member 35 is not provided on the upper surface 33B of the pressing plate 33, the determination of step S112 is negative, and the process proceeds to step S116.

In step S116, the ultrasonography control unit 84 outputs a warning regarding that the member 35 is not provided on the upper surface 33B of the pressing plate 33. The method for the ultrasonography control unit 84 to warn of the member 35 being not provided is not particularly limited. However, for example, an aspect in which characters indicating the warning are displayed on the display unit 58 of the console 12 or sound indicating the warning is output from the display unit 58 in a case where the display unit 58 includes a speaker or the like may be adopted.

In step S118, the ultrasonography control unit 84 performs control of prohibiting the capture of an ultrasound image, and the process returns to step S112. As an example, the ultrasonography control unit 84 of the embodiment outputs information indicating that the capture of an ultrasound image is prohibited to the ultrasonography apparatus 16. In a case where the user inputs an instruction to output ultrasonic waves using the ultrasound probe 65, the control unit 60 of the ultrasonography apparatus 16 causes the display unit 68 of the ultrasonography apparatus 16 to display an error message and does not receive an output instruction to prohibit the capture of an ultrasound image.

On the other hand, in a case where the member 35 is provided on the upper surface 33B of the pressing plate 33, the determination of step S112 is affirmative, and the process proceeds to step S114.

In step S114, the ultrasonography control unit 84 determines whether the coupling material 90 is provided between the pressing plate 33 and the member 35 on the basis of the detection result of the imaging member detection unit 80 as described above. In a case where the coupling material 90 is not provided between the pressing plate 33 and the member 35, the determination of step S114 is negative, and the process proceeds to step S118. On the other hand, in a case where the coupling material 90 is provided between the pressing plate 33 and the member 35, the determination of step S114 is affirmative, and the process proceeds to step S120.

In step S120, the ultrasonography control unit 84 determines whether to end the capture of an ultrasound image. As an example, in the medical imaging system 1 of the embodiment, in a case where the capture of an ultrasound image is ended, the user inputs information indicating that the capture of an ultrasound image is ended, through the operation unit 66 of the ultrasonography apparatus 16. The information indicating that the capture of an ultrasound image is ended, which has been input by the user, is transmitted from the ultrasonography apparatus 16 to the mammography apparatus 10. In a case where the information indicating that the capture of an ultrasound image is ended is received from the ultrasonography apparatus 16, the ultrasonography control unit 84 of the mammography apparatus 10 determines that the capture of the ultrasound image is ended. Until the capture of an ultrasound image is ended, the determination of step S120 is negative. On the other hand, in a case where the capture of an ultrasound image is ended, the determination of step S120 is affirmative, and the process proceeds to step S122.

In step S122, the ultrasonography control unit 84 allows the release of the pressing of the breast by the pressing plate 33, and then ends the present imaging control process. As an example, in the mammography apparatus 10 of the embodiment, until the ultrasonography control unit 84 allows the release of the pressing of the breast by the pressing plate 33, the pressing plate 33 is not moved even in a case where the user inputs an instruction to release the pressing (to move the pressing plate 33 in the pressing release direction) through the operation unit 56 or the like, except in case of emergency.

As described above, the imaging member 34 of each embodiment comprises the pressing plate 33 and the member 35. The pressing plate 33 presses the breast of the subject. The member 35 includes the upper surface 35B on which the acoustic matching member 92 having fluidity is provided, and the lower surface 35D on a side opposite to the upper surface 35B is provided on the upper surface 33B of the pressing plate 33, which is on a side opposite to a surface that comes into contact with the breast, via the coupling material 90 having lower fluidity than the acoustic matching member 92.

Further, the mammography apparatus 10 comprises the radiography control unit 82 and the ultrasonography control unit 84. The radiography control unit 82 performs control of irradiating the breast, which is in the pressed state by the pressing plate 33 of the imaging member 34, with the radiation and causing the radiation detector 30 to capture a radiographic image of the breast. The ultrasonography control unit 84 performs control of causing the ultrasonography apparatus 16 to capture an ultrasound image of the breast in a state where the member 35 is provided on the upper surface 33B of the pressing plate 33 via the coupling material 90 having lower fluidity than the acoustic matching member 92 and the acoustic matching member 92 is provided on the upper surface 35B of the member 35.

In this manner, with the medical imaging system 1 of the embodiment, in a case where an ultrasound image is captured, the member 35 on which the acoustic matching member 92 is applied may be provided on the upper surface 33B of the pressing plate 33. Accordingly, since the removal of the acoustic matching member 92 is not required and a radiographic image can be continuously captured without replacing the pressing plate 33 instead of removing the acoustic matching member 92, it is possible to improve the imaging efficiency.

In addition, with the medical imaging system 1 of the embodiment, even if the acoustic matching member 92 is not directly applied on the upper surface 33B of the pressing plate 33, since the member 35 on which the acoustic matching member 92 may be applied may be provided on the upper surface 33B of the pressing plate 33 via the coupling material 90, the acoustic matching member 92 can be easily provided, and thereby the user convenience is improved. In addition, since preparation for capturing an ultrasound image is simplified and time for the preparation is shortened, the burden on the subject of which the breast is pressed is also reduced.

Further, since it is possible to easily remove the member 35 and the coupling material 90 provided on the pressing plate 33 as compared with a case where the acoustic matching member 92 which has been directly applied on the upper surface 33B of the pressing plate 33 is removed, it is possible to improve the user convenience.

In the embodiment, an aspect in which the radiography control unit 82 prohibits the capture of a radiographic image in a case where the member 35 is provided on the upper surface 33B of the pressing plate 33 has been described. However, the present disclosure is not limited to the aspect, and, for example, an aspect in which the capture of a radiographic image is allowed in a case where the member 35 is not provided on the upper surface 33B of the pressing plate 33 may be adopted. Similarly, in the embodiment, an aspect in which the ultrasonography control unit 84 prohibits the capture of an ultrasound image in a case where the member 35 is not provided on the upper surface 33B of the pressing plate 33 has been described. However, the present disclosure is not limited to the aspect, and, for example, an aspect in which the capture of an ultrasound image is allowed in a case where the member 35 is provided on the upper surface 33B of the pressing plate 33 may be adopted.

Further, the present disclosure is not limited to the embodiment, and an aspect in which the imaging member detection unit 80 further detects that the coupling material 90 is provided on the upper surface 33B of the pressing plate 33 may be adopted. An aspect in which the radiography control unit 82 prohibits the capture of a radiographic image in a case where the coupling material 90 is provided on the upper surface 33B of the pressing plate 33 on the basis of the detection result of the imaging member detection unit 80 may be adopted. In this case, it is possible to suppress that a radiographic image is captured in a state where the coupling material 90 used in the previous capture of an ultrasound image has been forgotten to be removed.

In the embodiment, an aspect in which a radiographic image is captured first in a case where both a radiographic image and an ultrasound image are captured has been described, but an aspect an ultrasound image is captured first may be adopted. In this case, since a radiographic image can be captured immediately in a case where the member 35 and the coupling material 90 are detached from the upper surface 33B of the pressing plate 33 without removing the acoustic matching member 92, it is possible to obtain higher effects.

Figure 11:
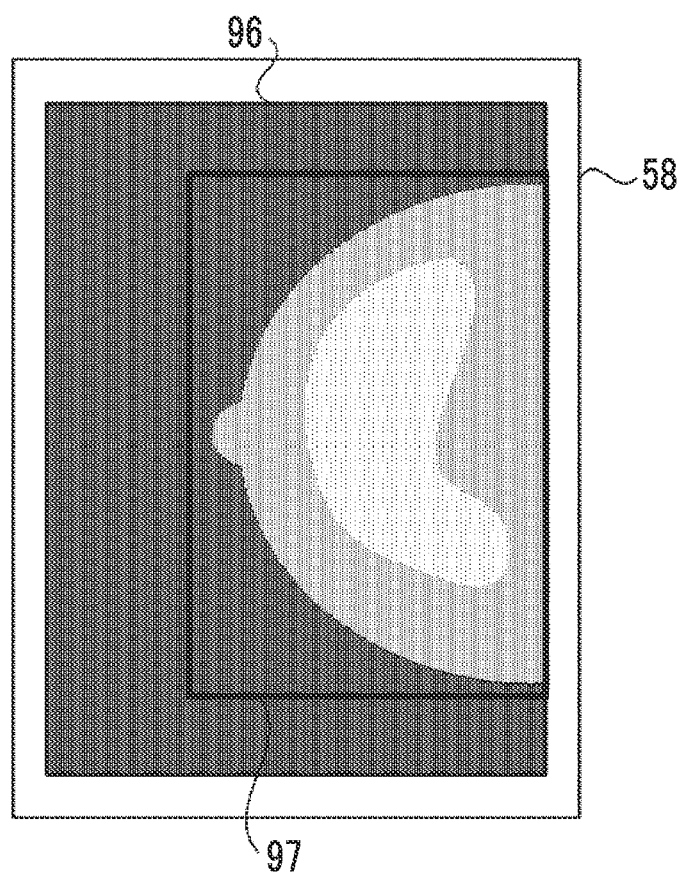
FIG. 11 is a diagram describing an example of a state where a radiographic image is displayed on a display unit in a state where an information image indicating an imaging range of an ultrasound image is added.

In a case where a radiographic image is captured first, it is preferable that the ultrasonography control unit 84 causes the display unit 58 of the console 12 to display a radiographic image 96 in a state where an information image 97 indicating the imaging range of the ultrasound image is added, as illustrated in FIG. 11. In this case, the ultrasonography control unit 84 may obtain the imaging range of the ultrasound image from the position and size of the upper surface 35B of the member 35 in advance.

Figure 12:
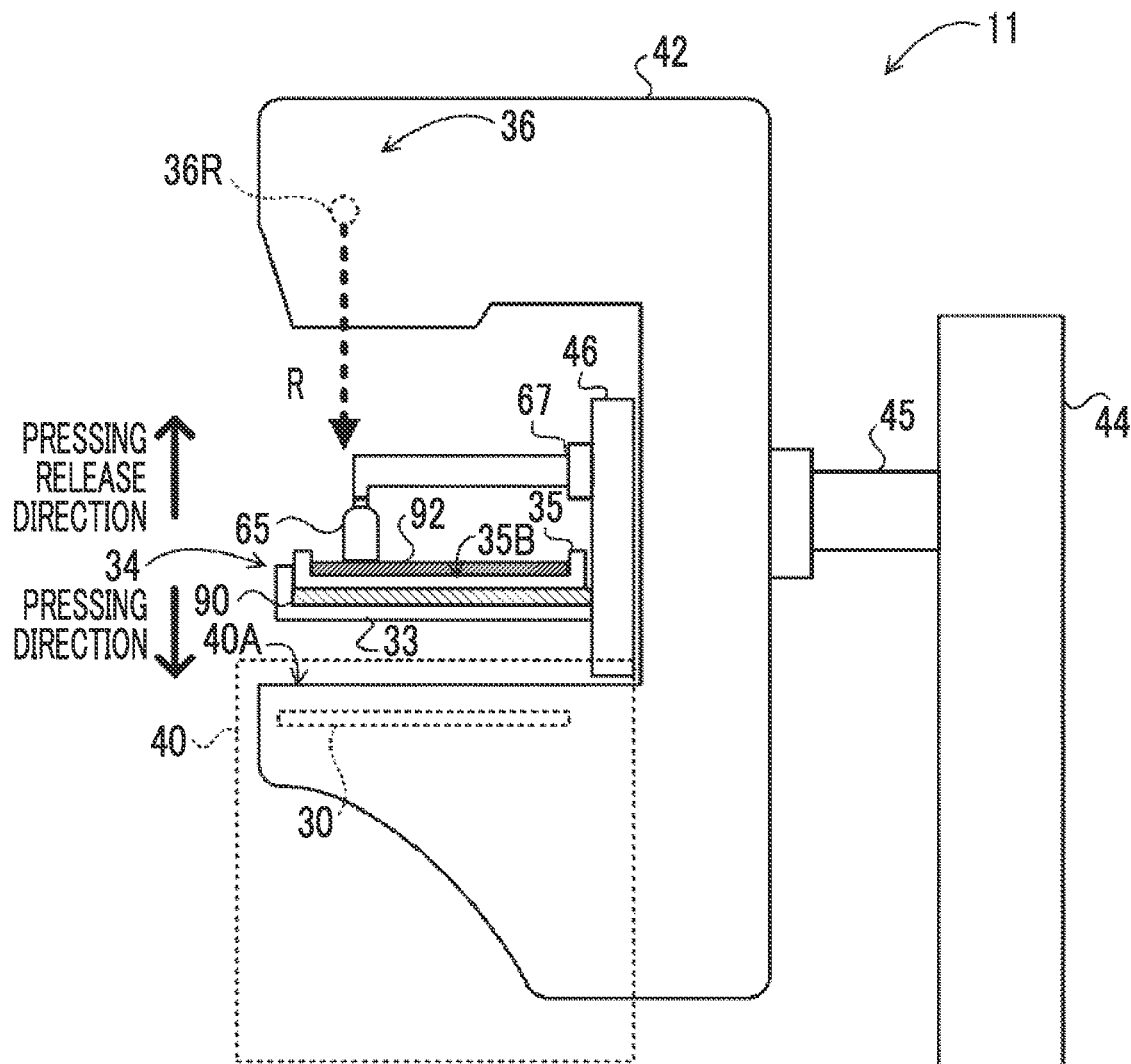
FIG. 12 is a side view illustrating an example of the appearance of a medical imaging apparatus of the embodiment.

In the embodiment, an aspect in which the mammography apparatus 10 and the ultrasonography apparatus 16 are separated has been described, but as illustrated in FIG. 12, the mammography apparatus 10 and the ultrasonography apparatus 16 may be integrated to form a medical imaging apparatus 11. In the medical imaging apparatus 11 illustrated in FIG. 12, the ultrasound probe 65 is moved along the upper surface (a surface opposite to the surface that comes into contact with the breast of the subject) 35B of the member 35 by a probe moving mechanism 67 and scans the breast with ultrasonic waves to automatically acquire an ultrasound image of the breast, so that an ultrasound image is automatically captured.

In the embodiment, an aspect in which the mammography apparatus 10 functions as the control device of the present disclosure has been described, but the apparatus functioning as the control device of the present disclosure is not limited to the mammography apparatus 10. For example, the console 12 or the like may function as the control device of the present disclosure, or the function of the control device of the present disclosure may be realized by a plurality of apparatuses such as the mammography apparatus 10 and the console 12.

In the above-described embodiments, for example, the following various processors can be used as the hardware structure of processing units executing various processes such as the imaging member detection unit 80, the radiography control unit 82, and the ultrasonography control unit 84. The various processors include, for example, a programmable logic device (PLD) that is a processor of which the circuit configuration can be changed after manufacture, such as a field-programmable gate array (FPGA), and a dedicated electric circuit that is a processor having a dedicated circuit configuration designed to execute a specific process, such as an application specific integrated circuit (ASIC), in addition to the CPU that is a general-purpose processor which executes software (program) to function as various processing units as described above.

One processing unit may be configured by one of the various processors or a combination of the same or different kinds of two or more processors (for example, a combination of a plurality of FPGAs or a combination of a CPU and an FPGA). In addition, a plurality of processing units may be configured by one processor.

A first example of the configuration in which a plurality of processing units are configured by one processor is an aspect in which one processor is configured by a combination of one or more CPUs and software as typified by a computer such as a client or a server, and this processor functions as a plurality of processing units. A second example of the configuration is an aspect in which a processor fulfilling the functions of the entire system including a plurality of processing units by one integrated circuit (IC) chip as typified by a system on chip (SoC) or the like is used. As such, various processing units are configured by using one or more of the various processors as a hardware structure.

In addition, specifically, an electric circuit (circuitry) obtained by combining circuit elements, such as semiconductor elements, can be used as the hardware structure of the various processors.

In the above-described embodiments, an aspect in which the imaging control processing program 21 is stored (installed) in the ROM 20B in advance has been described. However, the present disclosure is not limited thereto. The imaging control processing program 21 may be provided by being recorded in a recording medium, such as a compact disc read only memory (CD-ROM), a digital versatile disc read only memory (DVD-ROM), or a universal serial bus (USB) memory. In addition, the imaging control processing program 21 may be downloaded from an external device through a network.

For example, the configurations and operations of the medical imaging system 1, the radiography system 2, the mammography apparatus 10, the ultrasonography apparatus 16, and the like described in the above-described embodiments are illustrative and may be changed according to the situation, without departing from the scope of the invention. It goes without saying that the above-described embodiments can be combined appropriately.

What is claimed is:

1. A control device comprising:
    a radiography control unit configured to cause irradiation of a breast with radiation and cause a radiation detector to capture a radiographic image of the breast, wherein the breast is in a state of being pressed by a pressing member of an imaging member that includes:
        the pressing member, and
        an ultrasonography member that has a first surface on which an acoustic matching member having fluidity is provided; and
    an ultrasonography control unit configured to cause an ultrasonography apparatus to capture an ultrasound image of the breast, in a state in which the ultrasonography member is on a second surface of the pressing member that is on a side of the pressing member opposite to a surface that contacts the breast, via a coupling material having lower fluidity than the acoustic matching member provided on the first surface of the ultrasonography member.

2. The control device according to claim 1, wherein the radiography control unit is configured to prohibit capture of the radiographic image in a case in which the ultrasonography member is on the second surface of the pressing member.

3. The control device according to claim 1, wherein the radiography control unit is configured to warn against capture of the radiographic image in a case in which the ultrasonography member is on the second surface of the pressing member.

4. The control device according to claim 1, wherein the radiography control unit is configured to prohibit providing the ultrasonography member on the second surface of the pressing member, before capture of the radiographic image.

5. The control device according to claim 1, wherein the ultrasonography control unit is configured to prohibit capture of the ultrasound image in a case in which the ultrasonography member is not on the second surface of the pressing member.

6. The control device according to claim 1, wherein the ultrasonography control unit performs control of warning against capture of the ultrasound image in a case in which the ultrasonography member is not on the second surface of the pressing member.

7. The control device according to claim 1, wherein the ultrasonography control unit is configured to prohibit capture of the ultrasound image in a case in which the coupling material is not provided between the ultrasonography member and the second surface of the pressing member.

8. A control method executed by a computer, the control method comprising:
    causing irradiation of a breast with radiation and causing a radiation detector to capture a radiographic image of the breast, wherein the breast is in a state of being pressed by a pressing member of an imaging member that includes:
        the pressing member, and
        an ultrasonography member that has a first surface on which an acoustic matching member having fluidity is provided; and
    causing an ultrasonography apparatus to capture an ultrasound image of the breast, in a state in which the ultrasonography member is provided on a second surface of the pressing member that is on a side of the pressing member opposite to a surface that contacts the breast, via a coupling material having lower fluidity than the acoustic matching member provided on the first surface of the ultrasonography member.

9. A non-transitory computer readable medium storing a control program executable by a computer to perform a process, the process comprising:
    causing irradiation of a breast with radiation and causing a radiation detector to capture a radiographic image of the breast, wherein the breast is in a state of being pressed by a pressing member of an imaging member that includes:
        the pressing member, and
        an ultrasonography member that has a first surface on which an acoustic matching member having fluidity is provided; and
    causing an ultrasonography apparatus to capture an ultrasound image of the breast, in a state in which the ultrasonography member is provided on a second surface of the pressing member that is on a side of the pressing member opposite to a surface that contacts the breast, via a coupling material having lower fluidity than the acoustic matching member provided on the first surface of the ultrasonography member.

* * * * *